(12) United States Patent
Kijima

(10) Patent No.: US 9,145,579 B2
(45) Date of Patent: Sep. 29, 2015

(54) ANALYZING DEVICE

(71) Applicant: Panasonic Corporation, Kadoma-shi, Osaka (JP)

(72) Inventor: Tomohiro Kijima, Ehime (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 0 days.

(21) Appl. No.: 14/114,994

(22) PCT Filed: Jun. 24, 2013

(86) PCT No.: PCT/JP2013/003913
§ 371 (c)(1),
(2) Date: Oct. 31, 2013

(87) PCT Pub. No.: WO2014/017018
PCT Pub. Date: Jan. 30, 2014

(65) Prior Publication Data
US 2014/0073041 A1    Mar. 13, 2014

(30) Foreign Application Priority Data
Jul. 24, 2012  (JP) .................................. 2012-163387

(51) Int. Cl.
*B01L 3/00* (2006.01)
*G01N 9/30* (2006.01)
(Continued)

(52) U.S. Cl.
CPC ............. *C12Q 1/60* (2013.01); *B01L 3/502753* (2013.01); *G01N 33/491* (2013.01); *B01L 3/50273* (2013.01); *B01L 2200/10* (2013.01); *B01L 2200/16* (2013.01); *B01L 2300/0803* (2013.01); *B01L 2300/087* (2013.01); *B01L 2400/0409* (2013.01); *B01L 2400/0688* (2013.01); *G01N 2035/00158* (2013.01); *G01N 2035/00495* (2013.01); *G01N 2035/0403* (2013.01); *G01N 2035/0449* (2013.01)

(58) Field of Classification Search
None
See application file for complete search history.

(56) References Cited

U.S. PATENT DOCUMENTS 5,242,606 A * 9/1993 Braynin et al. ............... 210/787
5,304,348 A * 4/1994 Burd et al. ...................... 422/72
(Continued)

FOREIGN PATENT DOCUMENTS

CN     100407368 C     7/2008
CN     102099688 A     6/2011
(Continued)

OTHER PUBLICATIONS

Extended European Search Report, Jun. 22, 2015; European Patent Application No. 13822288.0 (8 pages).

*Primary Examiner* — Jennifer Wecker
(74) *Attorney, Agent, or Firm* — Hamre, Schumann, Mueller & Larson, P.C.

(57) ABSTRACT

A feature of an analyzing device is that a peeling portion (14) extending outward is partially connected to the outer edge of a reagent retaining portion (13) that is formed in a separating chamber (6) provided in a main unit case (2) and retains a reagent (8). With this configuration, when a droplet of the reagent (8) is dried and fixed on the reagent retaining portion (13), an external force applied to the droplet can be smaller than that on other portions. The dried reagent (8) starts shrinking from the position of the peeling portion 14. At the completion of drying, the reagent (8) can be smaller in size than the reagent retaining portion (13) in plan view and can be larger in thickness than the related art.

6 Claims, 17 Drawing Sheets

(51) Int. Cl.
   *G01N 1/10*   (2006.01)
   *C12Q 1/60*   (2006.01)
   *G01N 33/49*  (2006.01)
   *G01N 1/18*    (2006.01)
   *G01N 35/00*   (2006.01)
   *G01N 35/04*   (2006.01)

(56)              References Cited

U.S. PATENT DOCUMENTS

| | | | |
|---|---|---|---|
| 7,510,093 | B2 | 3/2009 | Aoki et al. |
| 2002/0045270 | A1 | 4/2002 | Schurenberg et al. |
| 2004/0197921 | A1 | 10/2004 | Schurenberg et al. |
| 2005/0025880 | A1 | 2/2005 | Masuda |
| 2006/0037935 | A1 | 2/2006 | Aoki et al. |
| 2006/0182654 | A1* | 8/2006 | Cumberland et al. .......... 422/56 |
| 2007/0125942 | A1* | 6/2007 | Kido .............................. 250/284 |
| 2009/0023201 | A1* | 1/2009 | Hongo et al. .............. 435/287.2 |
| 2009/0301227 | A1 | 12/2009 | Hattori et al. |
| 2011/0117665 | A1* | 5/2011 | Saiki et al. ..................... 436/164 |
| 2011/0126646 | A1 | 6/2011 | Saiki et al. |
| 2011/0186466 | A1* | 8/2011 | Kurowski et al. .......... 206/524.6 |
| 2013/0266480 | A1 | 10/2013 | Kimura et al. |

FOREIGN PATENT DOCUMENTS

| | | |
|---|---|---|
| JP | H08-501264 | 2/1996 |
| JP | H10-501340 | 2/1998 |
| JP | 2005-028275 | 2/2005 |
| JP | 2005-028279 | 2/2005 |
| JP | 2006-060076 | 3/2006 |
| JP | 2009-058820 | 3/2009 |
| JP | 2009-098039 | 5/2009 |
| JP | 2010-210531 | 9/2010 |
| JP | 2012-122977 | 6/2012 |
| WO | WO 95/33986 | 12/1995 |
| WO | WO 2007/066518 | 6/2007 |
| WO | 2011/032941 | 3/2011 |

* cited by examiner

ANALYZING DEVICE

TECHNICAL FIELD

The present invention relates to an analyzing device used for analyzing a liquid collected from a living organism and so on.

BACKGROUND ART

An analyzing device contains a feed passage having a microchannel structure for transporting a liquid to be tested from a sample feed opening to a measuring chamber, a separating chamber containing a reagent reacting with components to be tested, the measuring chamber connected to the separating chamber via a first branch, and a reservoir connected to the separating chamber via a second branch.

The analyzing device is rotated or pivoted about a rotating shaft after collecting a liquid to be tested from the sample feed opening. Thus, the liquid in a mixing cavity is mixed and centrifuged, specific components are separated by the reagent in the separating chamber, the liquid treated in the separating chamber is transported to the measuring chamber, and then the analyzing device is used for reading for accessing the liquid in the measuring chamber.

CITATION LIST

Patent Literatures

Patent Literature 1: National Publication of International Patent Application No. 10-501340
Patent Literature 2: Japanese Patent Laid-Open No. 2010-210531

SUMMARY OF INVENTION

Technical Problem

Specifically, a liquid such as blood to be tested is collected into a main unit case from the sample feed opening and then is supplied to the separating chamber through the feed passage. In the separating chamber, the sample is treated with the reagent into two samples. One of the samples is supplied to the measuring chamber through the first branch while the other sample is supplied to the reservoir through the second branch. The measuring chamber is irradiated with, for example, light and a quantity of transmitted light is measured to analyze the blood.

For example, HDL cholesterol in blood is generally called good cholesterol. When a liquid extracted from blood is supplied to the separating chamber to measure the components of the liquid, a reagent placed in a dry state in advance separates the sample to measure the HDL cholesterol.

Unfortunately, if the analyzing device is used at a high humidity, the reagent set in the separating chamber may absorb moisture and fluidize when the analyzing device is stored.

When the analyzing device is rotated at a high speed to apply a centrifugal force to the liquid in the analyzing device, the reagent fluidized by moisture absorption may flow into one of the measuring chamber and the reservoir before the liquid to be tested reaches the separating chamber.

Consequently, specific components in the separating chamber may not be separated so as to cause varying measured values in the measuring chamber, reducing the reliability of measurement under the present circumstances.

An object of the present invention is to provide an analyzing device that can more reliably retain a reagent than in a conventional technique until a liquid to be tested reaches a separating chamber, even if the analyzing device is used at a high humidity.

Solution to Problem

The analyzing device of the present invention includes a main unit case containing a feed passage having a microchannel structure for transporting a liquid to be tested to a measuring chamber from a sample feed opening provided on the main unit case, a separating chamber containing a reagent placed for treating a component to be tested in the liquid to be tested, a reservoir connected to the separating chamber via a first branch, and a measuring chamber connected to the separating chamber via a second branch, the analyzing device being used for centrifugally transporting the liquid treated in the separating chamber by the reagent to the measuring chamber, and for reading for accessing the liquid in the measuring chamber, the reagent being placed on a reagent retaining portion whose outer edge is partially connected to a peeling portion extending outward.

Advantageous Effect of Invention

With this configuration, the outer edge of the reagent retaining portion is partially connected to the peeling portion. Thus, a retaining force applied to a droplet of the reagent can be partially eliminated at a portion connected to the peeling portion. When the reagent is dropped to the reagent retaining portion, the reagent spreads to the outer edge of the reagent retaining portion and then starts shrinking in a dry state. During the shrinkage, at a portion of the peeling portion connected to the outer edge of the reagent retaining portion, the outer end of the reagent is not in contact with the outer edge of the reagent retaining portion. The outer end of the reagent starts shrinking from the portion into the reagent retaining portion. The reagent continues to shrink such that the outer end of the reagent partially in contact with the outer edge of the reagent retaining portion is peeled into the reagent retaining portion, drying the reagent into a smaller size with a certain thickness.

Even if the small dried reagent with a certain thickness is used at a high humidity, only the surface of the reagent is fluidized by absorbed moisture but the inner part of the reagent is not fluidized by the moisture. Thus, the reagent does not accidentally flow out of the separating chamber because of a centrifugal force.

Consequently, the reagent reliably treats a sample so as to obtain stable measured values in the measuring chamber, increasing the reliability of measurement.

BRIEF DESCRIPTION OF DRAWINGS

FIG. 4(*b*) is an enlarged view of a separating chamber of the main unit case.

FIG. 8(*b*) is a plan view of FIG. 8(*a*).

FIG. 9(*b*) is a plan view of FIG. 9(*a*).

FIG. 10(*b*) is a plan view of FIG. 10(*a*).

FIG. 11(*b*) is a plan view of FIG. 11(*a*).

FIG. 12(*b*) is an enlarged plan view of a principal part including rectangular peeling portions according to the second embodiment of the present invention.

FIG. 13(*b*) is an enlarged plan view of a principal part including triangular peeling portions according to the third embodiment of the present invention.

FIG. 13(*c*) is an enlarged plan view of a principal part including rectangular peeling portions according to the third embodiment of the present invention.

FIG. 17(*b*) is a plan view of FIG. 17(*a*).

FIG. 18(*b*) is a plan view of FIG. 18(*a*).

FIG. 19(*b*) is a plan view of FIG. 19(*a*).

FIG. 20(*b*) is a plan view of FIG. 20(*a*).

DESCRIPTION OF EMBODIMENTS

Embodiments of the present invention will be described below in comparison with the related art.

First Embodiment

Figure 1:
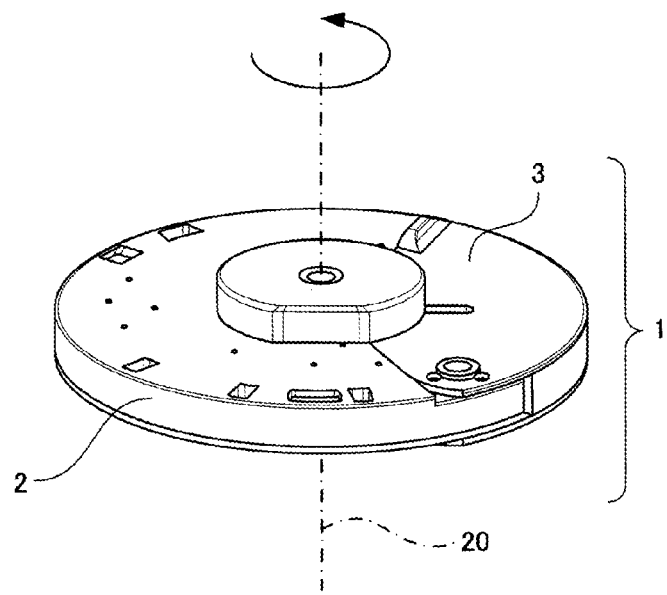
FIG. 1 is a perspective view of an analyzing device according to a first embodiment of the present invention.

FIG. 1 is a perspective view of a completed analyzing device.

The outside shape of an analyzing device 1 is circular and includes a main unit case 2 containing a measuring chamber, a separating chamber, and microchannels such as a flow path, and a cover 3 having one end pivotally supported by the main unit case 2. The analyzing device 1 with the closed cover 3 is circular in plan view.

Figure 2:
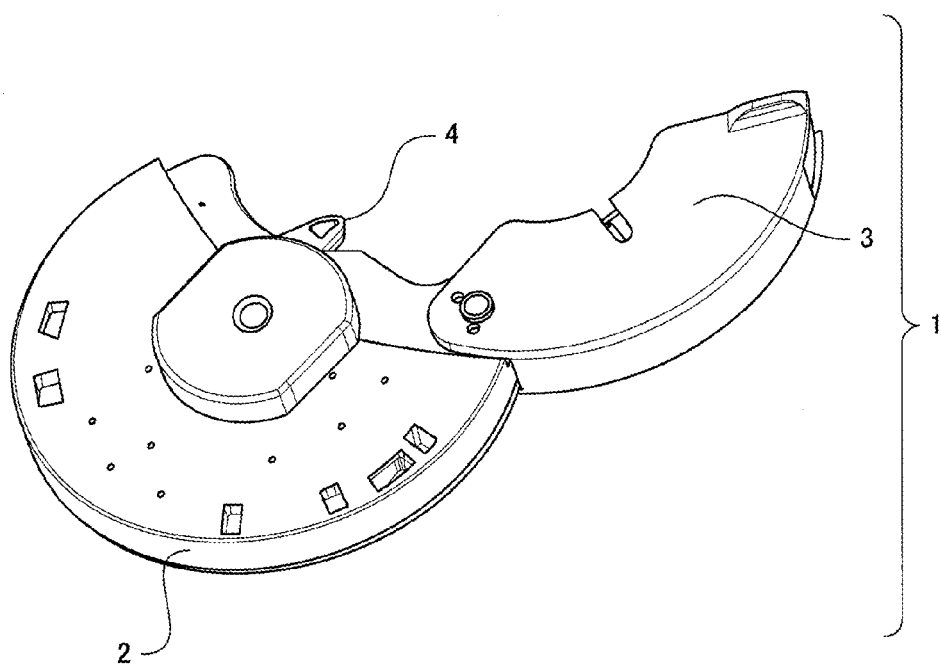
FIG. 2 is a perspective view showing an opened cover 3 according to the first embodiment of the present invention.

FIG. 2 illustrates a sample feed opening 4 exposed on the main unit case 2 by opening the cover 3. The sample feed opening 4 is a feed opening for feeding a sample, for example, blood into the main unit case 2.

Figure 3:
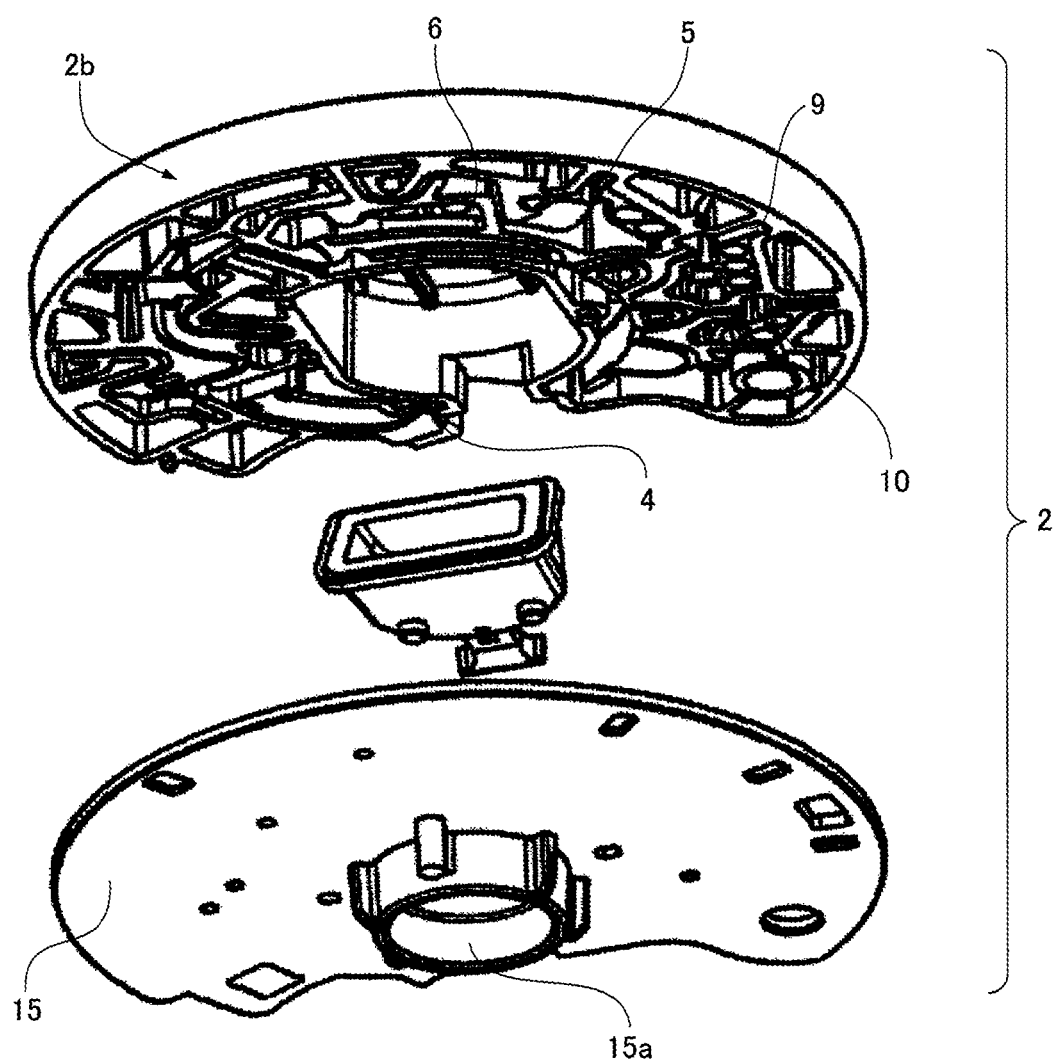
FIG. 3 is an exploded perspective view of the principal part of the analyzing device according to the first embodiment of the present invention.

FIG. 3 is an exploded perspective view of the main unit case 2. The main unit case 2 includes a base substrate 2*b* and a cover substrate 15 bonded under the base substrate 2*b*. The cover substrate 15 covers the openings of recessed portions formed on the underside of the base substrate 2*b*, thereby forming measuring chambers 5, 9, and 10, a separating chamber 6, and microchannels such as a flow path.

Under the cover substrate 15, a connected portion 15*a* is engaged with a rotating unit (not shown) for driving the analyzing device 1 about an axis 20.

The sample feed opening 4 and the measuring chamber 5 are connected as specifically described in Japanese Patent Laid-Open No. 2010-210531 filed by the inventors. Hence, only a basic part of the connected state will be discussed below.

Specifically, blood dropped into the sample feed opening 4 is drawn into the main unit case 2 by a capillary force of the flow path connected to the sample feed opening 4. The blood drawn into the main unit case 2 is separated into blood plasma and blood cells at a portion A of FIG. 4 by a centrifugal force. After that, only blood plasma is supplied to a mixing chamber B in FIG. 4. In the mixing chamber B, the blood plasma is mixed with a diluent supplied from a dilution chamber 7. A mixed solution of the diluent and the blood plasma is supplied to the separating chamber 6 from the mixing chamber B through the flow path. The separating chamber 6 contains a separating reagent 8. From a sample liquid supplied to the separating chamber 6, for example, HDL cholesterol of blood plasma components is separated by the separating reagent 8. In the separated state, the sample liquid is supplied to the measuring chamber 5 through a mixing chamber 17 and a second branch 19. The separating chamber 6 is connected to a reservoir 16 through the mixing chamber 17 and a first branch 18.

The measuring chamber 5 contains a reactant. The blood plasma substances supplied to the measuring chamber 5 react with the reactant. After that, the measuring chamber 5 is irradiated with light so as to measure the HDL cholesterol. The separating reagent 8 for measuring HDL cholesterol is a precipitation reagent. The reactant for measuring HDL cholesterol is an HDL enzyme liquid.

In the present embodiment, other substances are also measured in the measuring chamber 9 and the measuring chamber 10. In such measurement, flow paths are changed to supply blood plasma while bypassing the separating chamber 6, thereby performing various measurement. The specific structure is specifically described in Japanese Patent Laid-Open No. 2010-210531 filed by the inventors.

A feature of the present embodiment is separation of blood plasma substances (e.g., HDL cholesterol) in the separating chamber 6. The separating reagent 8 is disposed for this separation.

Figure 4A:
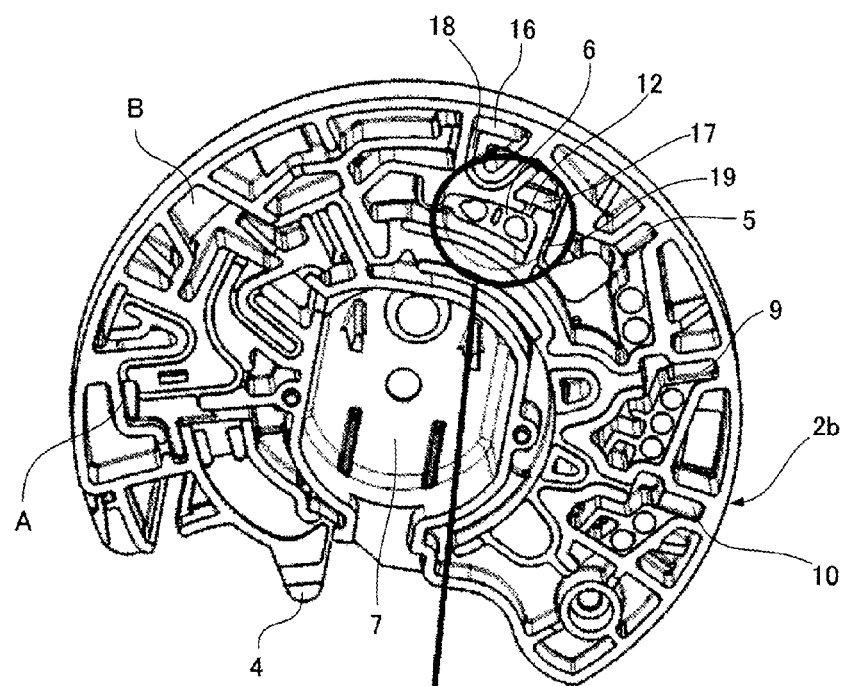
FIG. 4(*a*) is a perspective view illustrating a main unit case in the principal part from below according to the first embodiment of the present invention.
Figure 4B:
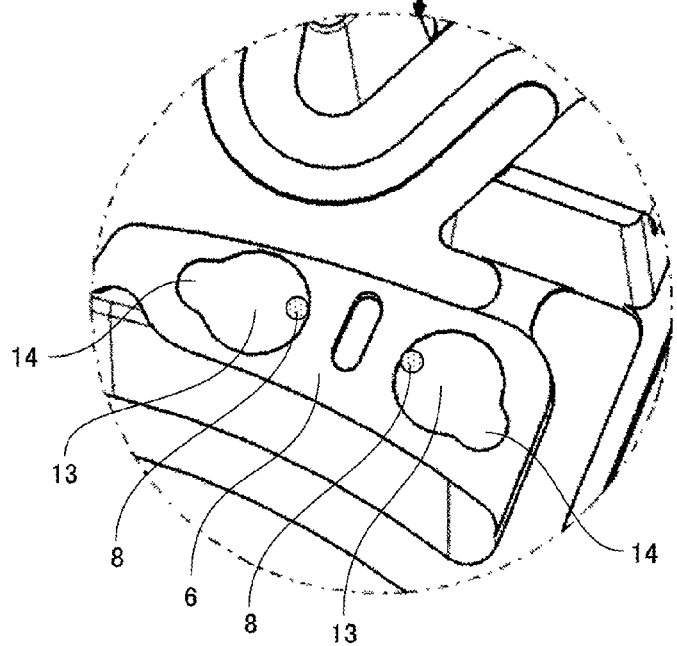
Figure 5:
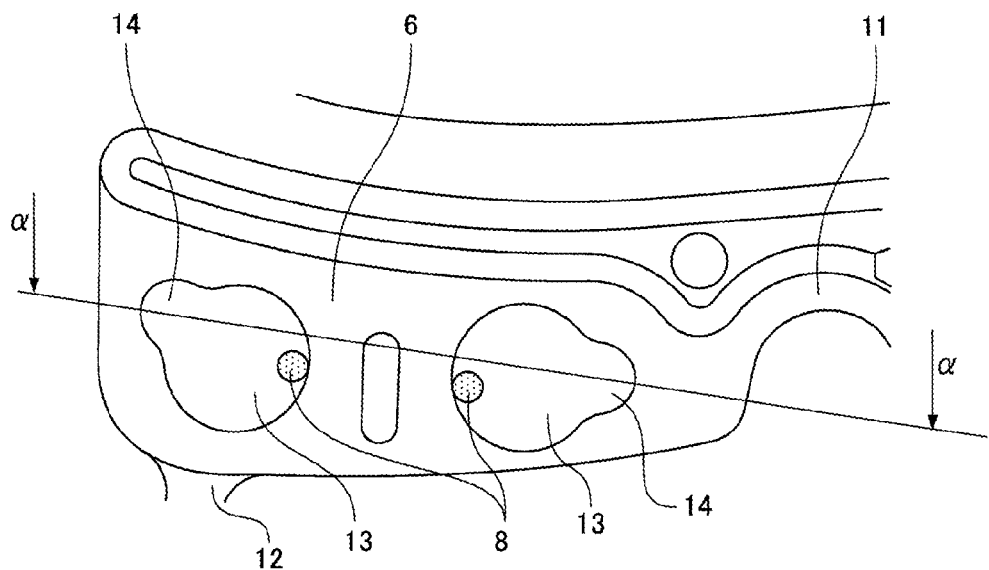
FIG. 5 is an enlarged plan view illustrating the separating chamber from below.
Figure 6:
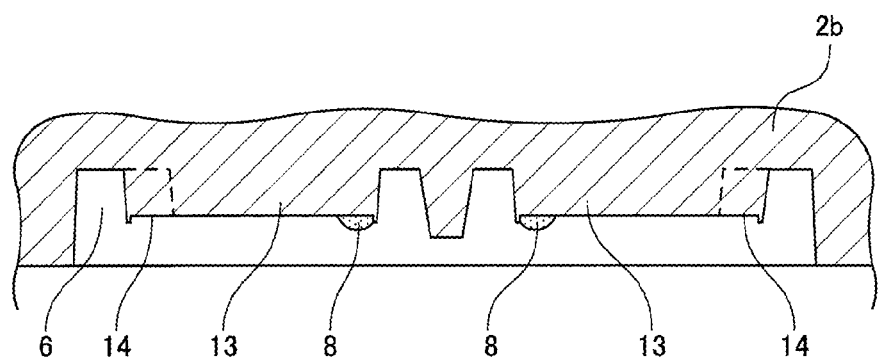
FIG. 6 is a cross-sectional view taken along the line α-α of FIG. 5.
Figure 7:
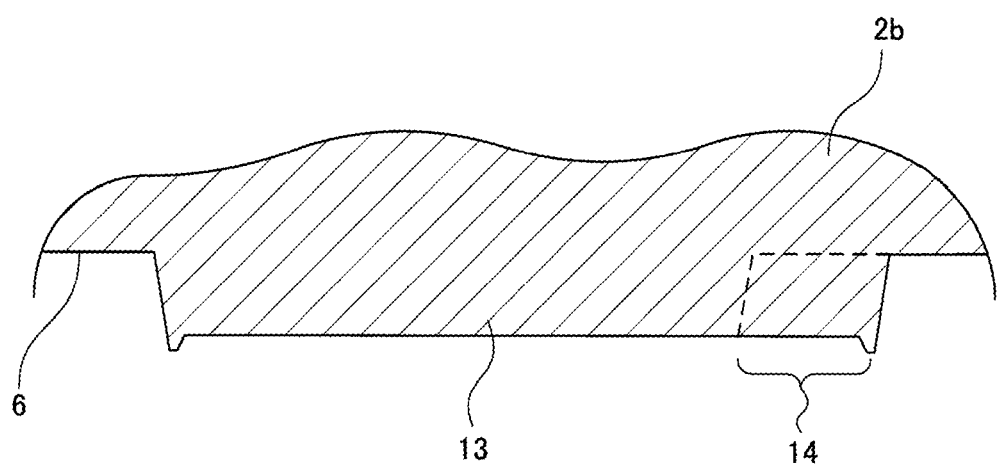
FIG. 7 is a partial enlarged view of a state before a reagent is retained on a reagent retaining portion of FIG. 6.

As shown in FIGS. 4(*b*), 5, and 6, in the separating chamber 6, reagent retaining portions 13 protruding downward are provided on a ceiling between an inlet 11 and an outlet 12. The reagent retaining portion 13 retains the separating reagent 8. Specifically, as understood from FIG. 5, the reagent retaining portion 13 is circular or substantially circular in plan view. The outer edge of the reagent retaining portion 13 is partially connected to a peeling portion 14 that extends outward and protrudes downward. The peeling portion 14 is one of circular and substantially circuit in plan view. The top surface of the peeling portion 14 is as high as the reagent retaining portion 13. The peeling portion 14 and the reagent retaining portion 13 are integrally resin-molded on the base substrate 2b.

The separating reagent 8 is disposed on the reagent retaining portions 13 in the steps of FIGS. 8 to 11.

Specifically, the cover substrate 15 in FIG. 3 is removed, and then the base substrate 2b is flipped to place the reagent retaining portions 13 face-up as illustrated in FIG. 8. The separating reagent 8 is dropped onto the reagent retaining portions 13.

Figure 8A:
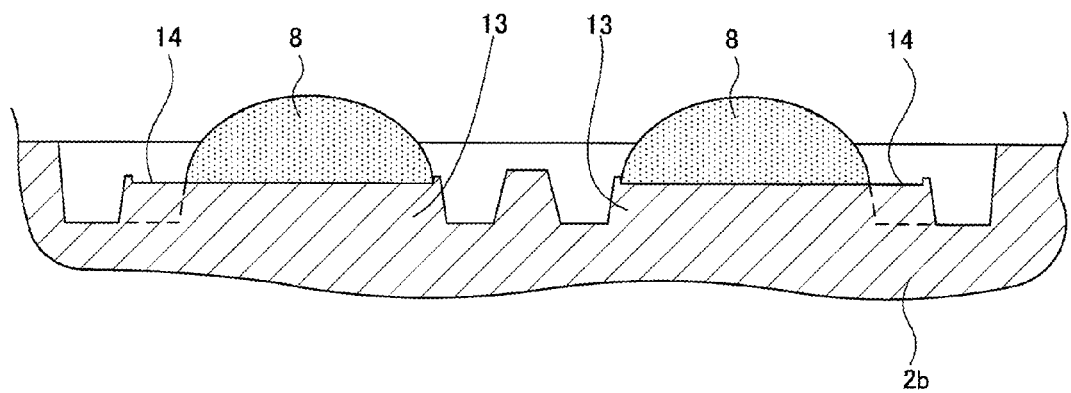
FIG. 8(*a*) is an enlarged cross-sectional view of a state immediately after the reagent is dropped according to the first embodiment of the present invention.
Figure 8B:
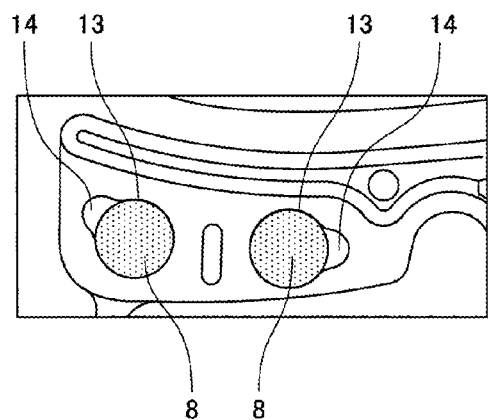

When the separating reagent 8 is dropped, as shown in FIG. 8(b), the separating reagent 8 spreads along the outer edge of the reagent retaining portion 13. It should be noted that the outer end of the separating reagent 8 spreading like a circle in FIG. 8(b) is partially located on the peeling portion 14. On the part of the peeling portion 14, the outer end of the underside of the separating reagent 8 is not in contact with the outer edge of the circular reagent retaining portion 13.

In other words, outside a portion where the peeling portion 14 is connected to the reagent retaining portion 13, the outer edge of the reagent retaining portion 13 applies a retaining force to the outer end of the droplet of the separating reagent 8, whereas at the portion where the peeling portion 14 is connected to the reagent retaining portion 13, the outer edge of the reagent retaining portion 13 does not apply a retaining force to the outer end of the droplet of the separating reagent 8.

Figure 9A:
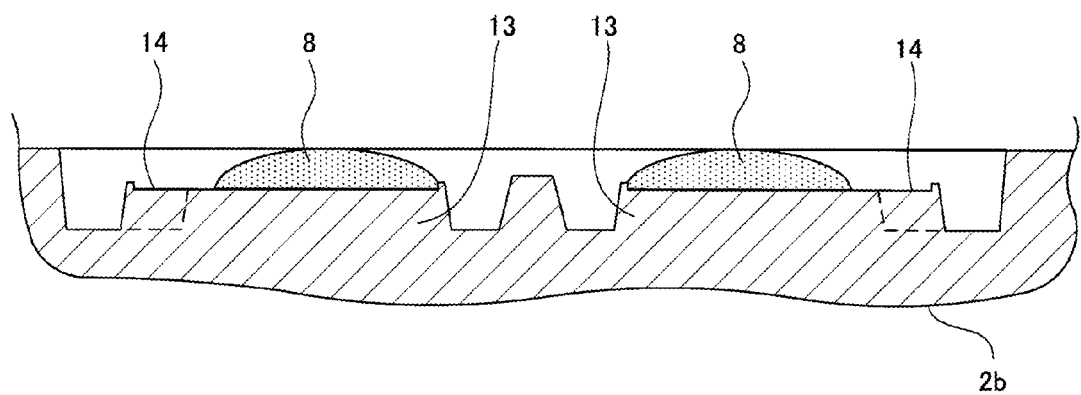
FIG. 9(*a*) is an enlarged cross-sectional view of the initial dried state of the reagent according to the first embodiment of the present invention.
Figure 9B:
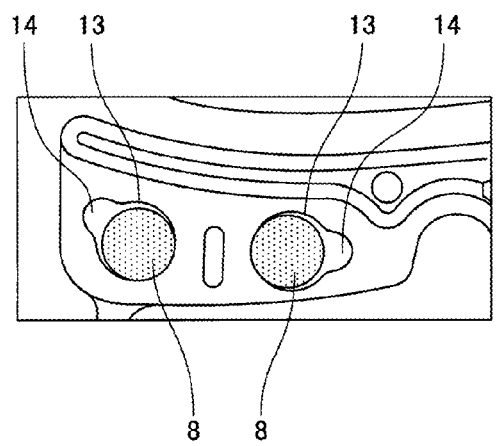
Figure 10A:
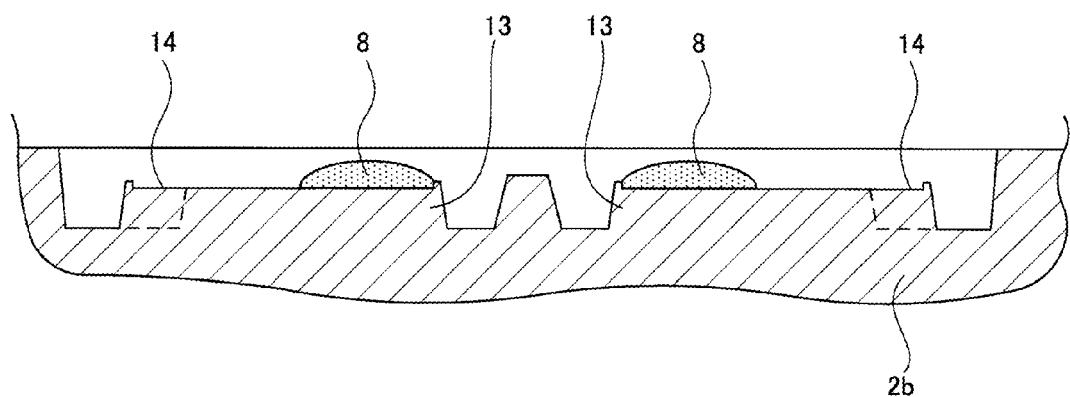
FIG. 10(*a*) is a cross-sectional view of the intermediate dried state of the reagent according to the first embodiment of the present invention.
Figure 10B:
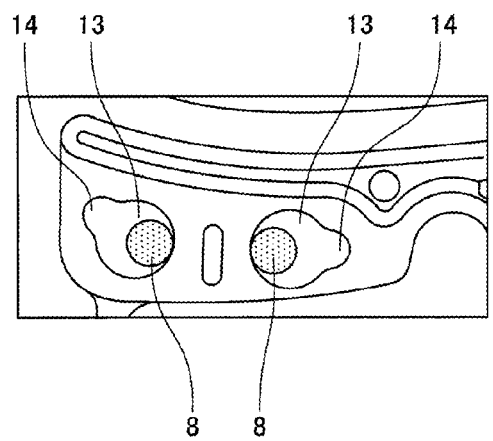
Figure 11A:
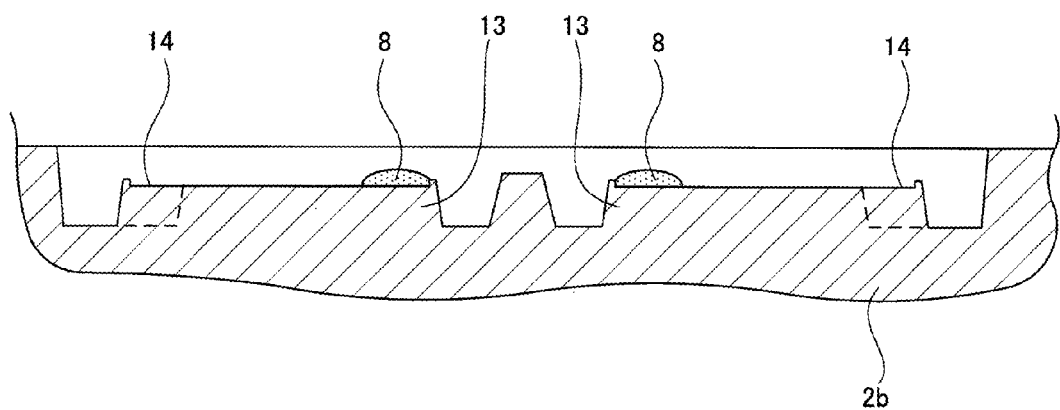
FIG. 11(*a*) is an enlarged cross-sectional view of the terminal dried state of the reagent according to the first embodiment of the present invention.
Figure 11B:
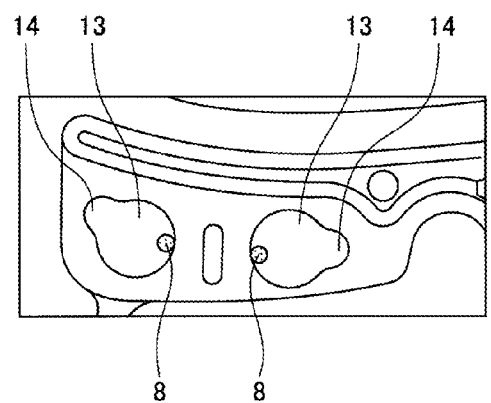

Thus, at the start of drying of the base substrate 2b with droplets of the separating reagents 8 in FIGS. 8(a) and 8(b), the dried droplet of the separating reagent 8 starts shrinking from a portion where the separating reagent 8 is not in contact with the outer edge of the circular reagent retaining portion 13. The separating reagent 8 is then kept dried in a drying period as illustrated in FIGS. 9 and 10; meanwhile, the shrinking separating reagent 8 is continued to be peeled into the reagent retaining portion 13 at a portion where the outer end of the separating reagent 8 is in contact with the outer edge of the reagent retaining portion 13. Consequently, as shown in FIG. 11, the dried separating reagent 8 has a small size and a certain thickness.

Thus, even if the analyzing device 1 is used at a high humidity, moisture is absorbed only on the surface of the dried separating reagent 8 with a small size and a certain thickness. The moisture fluidizing the surface does not reach the interior of the separating reagent 8. Hence, even a centrifugal force does not accidentally leak the separating reagent 8 to one of the measuring chamber 5 and the reservoir 16.

In this configuration, as shown in FIG. 4(a), the outlet 12 of the separating chamber 6 is connected to the mixing chamber 17 that is a part of the separating chamber 6. The mixing chamber 17 is connected to the reservoir 16 via the first branch 18 and is connected to the measuring chamber 5 via the second branch 19.

Thus, the feeding of a sample liquid into the separating chamber 6 allows reliable blood separation with the separating reagent 8. This can achieve stable measured values in the measuring chamber 5, leading to more reliable measurement.

Figure 14:
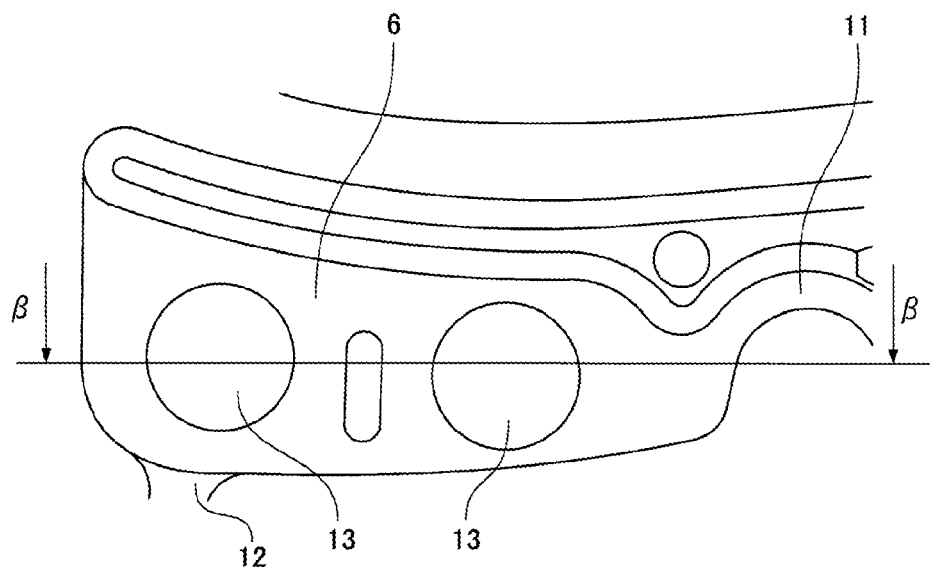
FIG. 14 is an enlarged plan view of a state before a reagent is retained on a reagent retaining portion of a separating chamber according to the related art.
Figure 15:
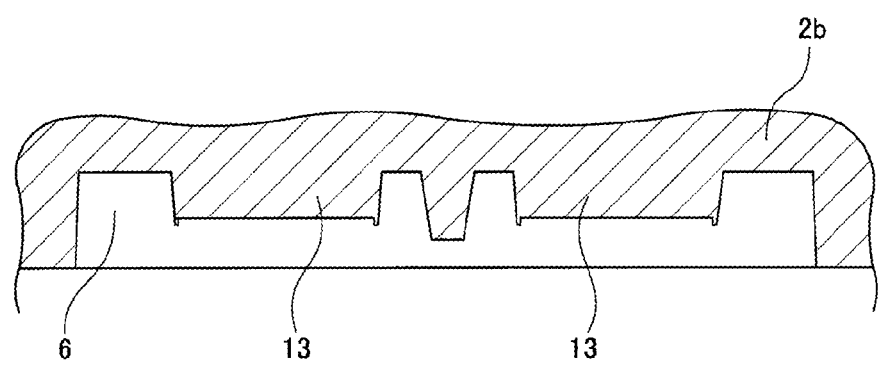
FIG. 15 is a cross-sectional view taken along the line β-β of FIG. 14.
Figure 16:
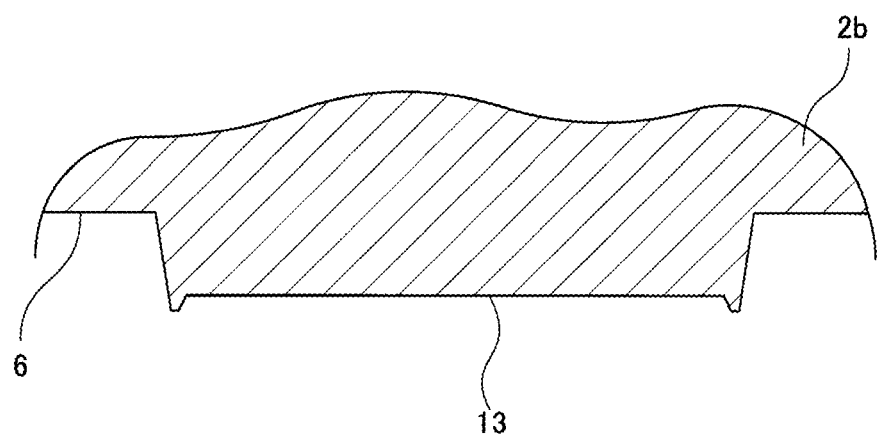
FIG. 16 is an enlarged view of a part of FIG. 15.

In the present embodiment, the reagent retaining portion 13 is partially connected to the peeling portion 14. FIGS. 14 to 16 illustrate a separating chamber 6 having a conventional structure in which the peeling portion 14 is not connected to the reagent retaining portion 13.

FIGS. 17 to 20 specifically illustrate this comparative example in which the separating reagent 8 is dropped to the reagent retaining portion 13 not connected to the peeling portion 14, and then the separating reagent 8 is dried thereon.

Figure 17A:
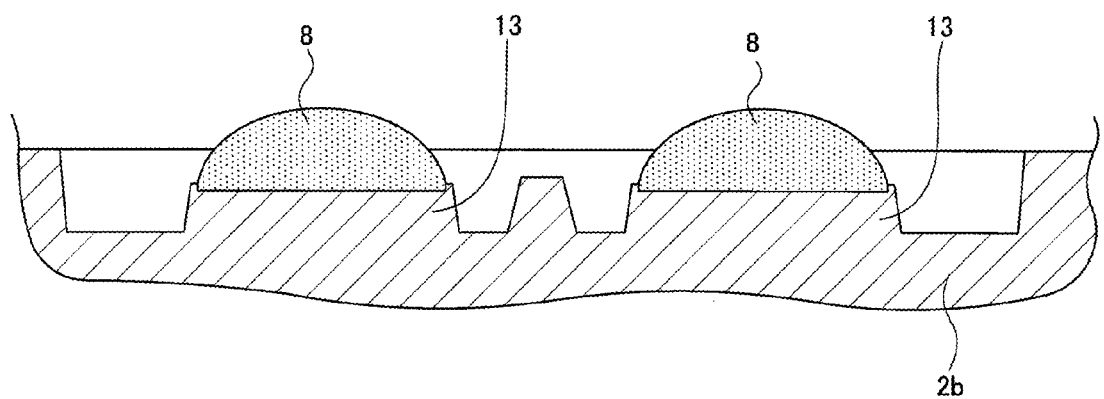
FIG. 17(*a*) is an enlarged cross-sectional view of a state immediately after the reagent is dropped according to the related art.
Figure 17B:
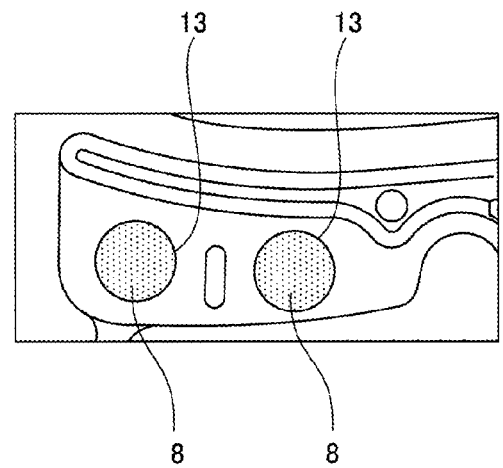
Figure 18A:
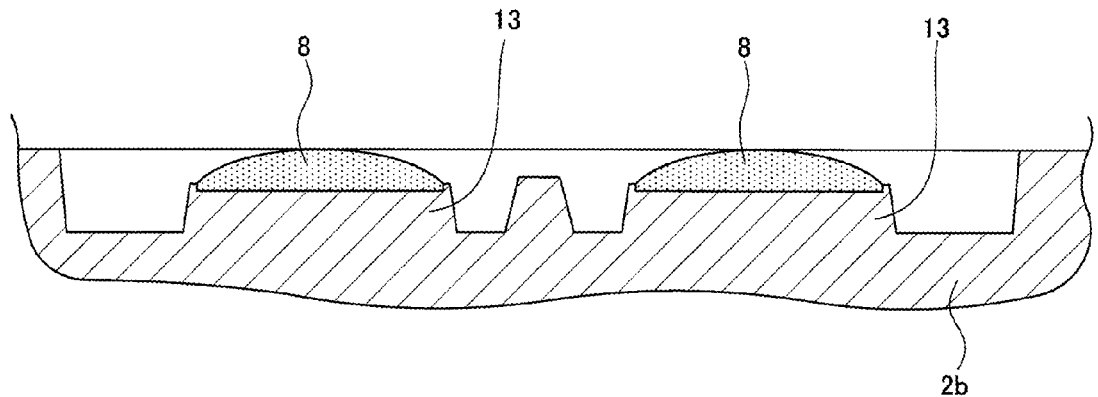
FIG. 18(*a*) is an enlarged cross-sectional view of the initial dried state of the reagent according to the related art.
Figure 18B:
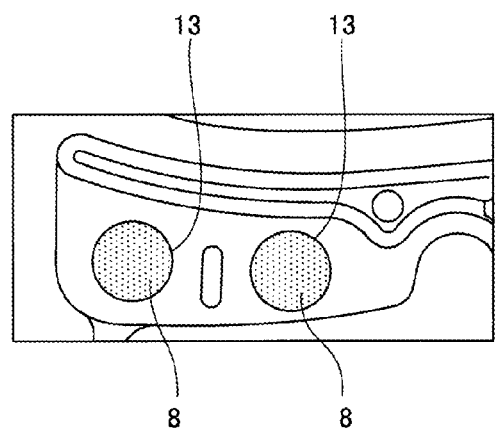
Figure 19A:
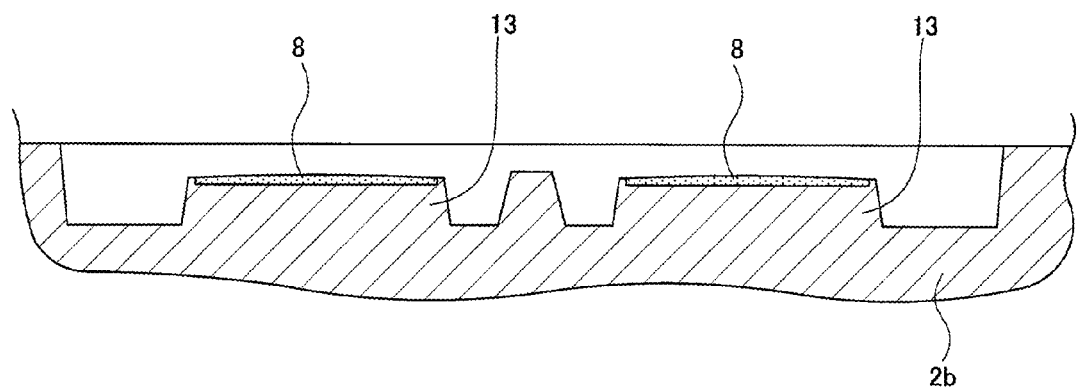
FIG. 19(*a*) is a cross-sectional view of the intermediate dried state of the reagent according to the related art.
Figure 19B:
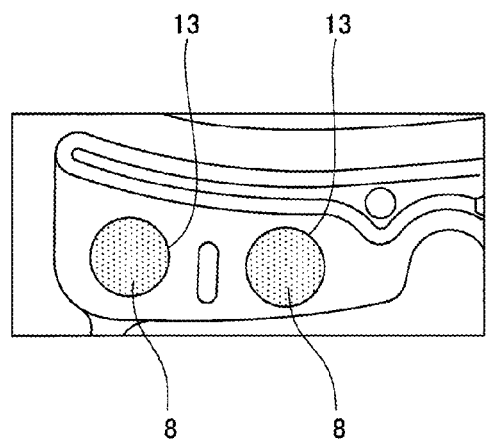
Figure 20A:
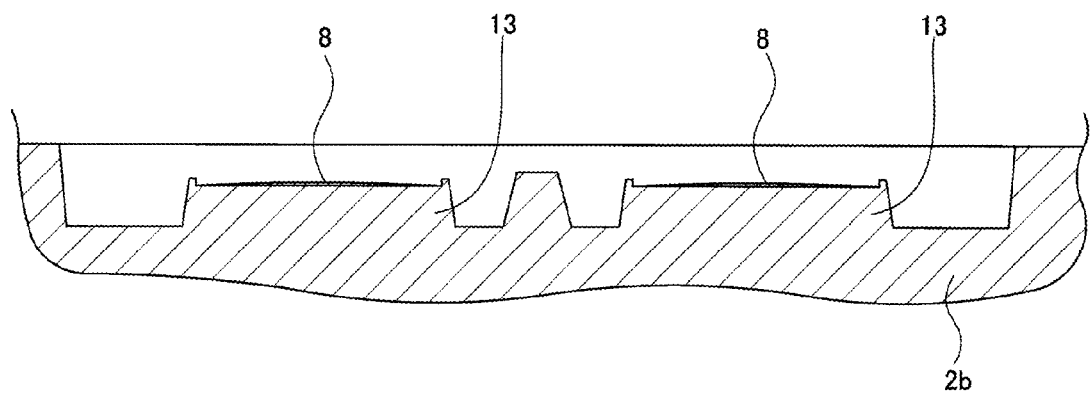
FIG. 20(*a*) is an enlarged cross-sectional view of the terminal dried state of the reagent according to the related art.
Figure 20B:
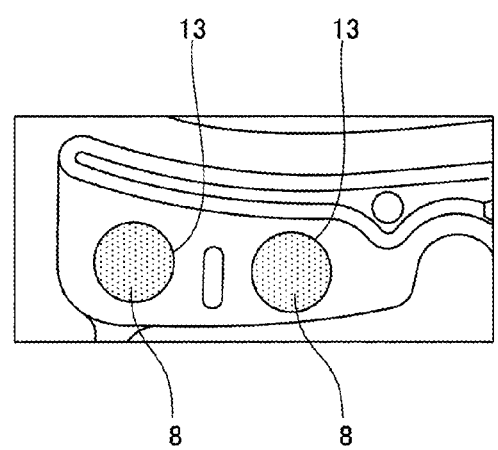

As illustrated in the comparative example, if a ceiling between the inlet 11 and the outlet 12 of the separating chamber 6 only has the reagent retaining portions 13 that protrudes downward and is circular in plan view, as shown in FIGS. 17(a) and 17(b), droplets of the separating reagent 8 on the reagent retaining portion 13 spread along the outer edge of the circular reagent retaining portions 13. It should be noted that as shown in FIG. 17(b), a retaining force is applied to the outer ends of the droplets of the separating reagent 8 by the outer edges of the reagent retaining portions 13. Thus, the droplets of the separating reagent 8 are dried such that the outer ends of the circular droplets of the separating reagent 8 are entirely kept in contact with the outer edges of the circular reagent retaining portions 13. During a drying period, the outside shape of the separating reagent 8 is as large as the outside shape of the reagent retaining portion 13 but is dried to have a smaller thickness as illustrated in FIGS. 18(a), 18(b), 19(a), and 19(b). Consequently, as shown in FIG. 20, the separating reagent 8 is dried with a large width and a small thickness.

If the separating reagent 8 dried with a large width and a small thickness is used at a high humidity, the overall surface of the separating reagent 8 is fluidized by absorbed moisture. Thus, the fluidized separating reagent 8 may be partially leaked to the reservoir 16 or the measuring chamber 5 via the mixing chamber 17 only by a centrifugal force.

The leakage of the separating reagent 8 does not allow reliable separation. Thus, unstably measured values are obtained in the measuring chamber 5, leading to less reliable measurement.

As is evident from the comparison between the embodiment of the present invention and the comparative example, in order to partially eliminate a retaining force applied to a droplet of the separating reagent 8 dried and fixed on a part of the reagent retaining portion 13, the peeling portion 14 extending outward is connected to the reagent retaining portion 13.

In the present embodiment, moisture does not reach the interior of the separating reagent 8 and thus the separating reagent 8 does not fluidize even at a high humidity. Hence, it is understood that even a centrifugal force does not accidentally leak the separating reagent 8 to one of the measuring chamber 5 and the reservoir 16.

The reagent retaining portions 13 protruding downward from the ceiling of the separating chamber 6 may be recessed upward from the ceiling surface of the separating chamber 6. The reagent retaining portions 13 are provided on the ceiling of the separating chamber 6 to smoothly pass a sample liquid on the floor surface of the separating chamber 6.

Second Embodiment

Figure 12A:
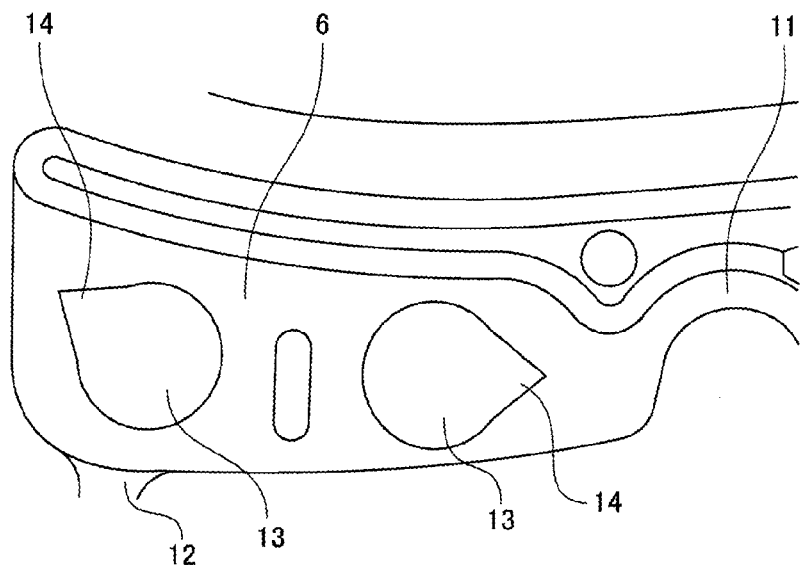
FIG. 12(*a*) is an enlarged plan view of a principal part including triangular peeling portions according to a second embodiment of the present invention.
Figure 12B:
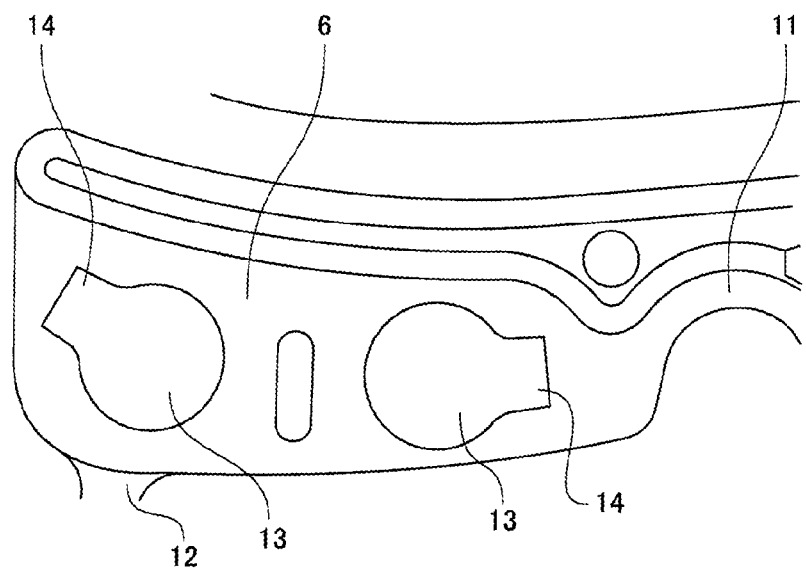

In the first embodiment, the outer edge of the reagent retaining portion 13 is partially connected to the circular or substantially circular peeling portion 14. As shown in FIG. 12(a), the outer edge of a reagent retaining portion 13 may be partially connected to one of a triangular and substantially triangular peeling portion 14. As shown in FIG. 12(b), the outer edge of the reagent retaining portion 13 may be partially connected to one of a rectangular and substantially rectangular peeling portion 14.

Third Embodiment

Figure 13A:
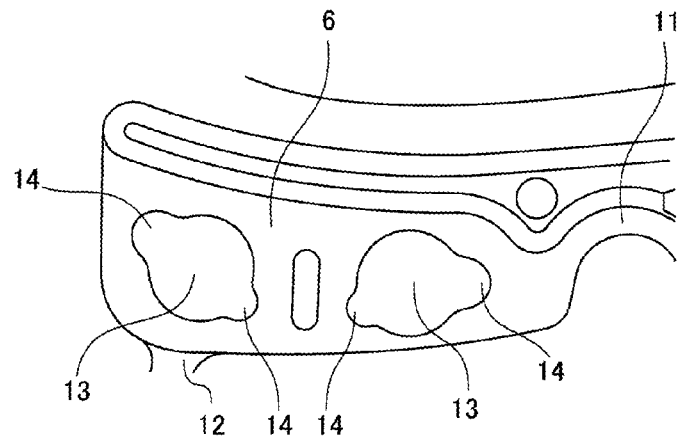
FIG. 13(*a*) is an enlarged plan view of a principal part including circular peeling portions according to a third embodiment of the present invention.
Figure 13B:
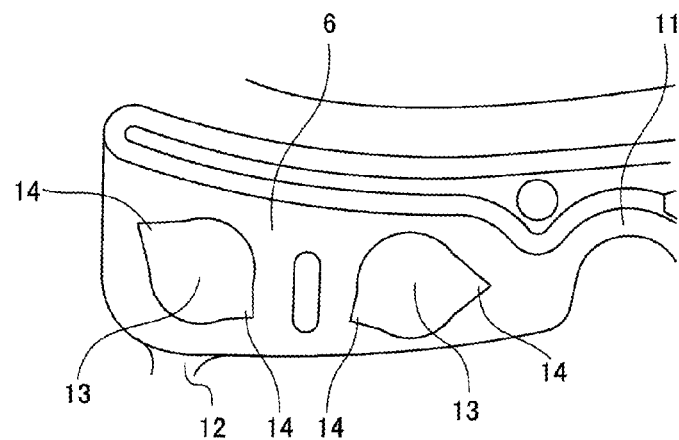
Figure 13C:
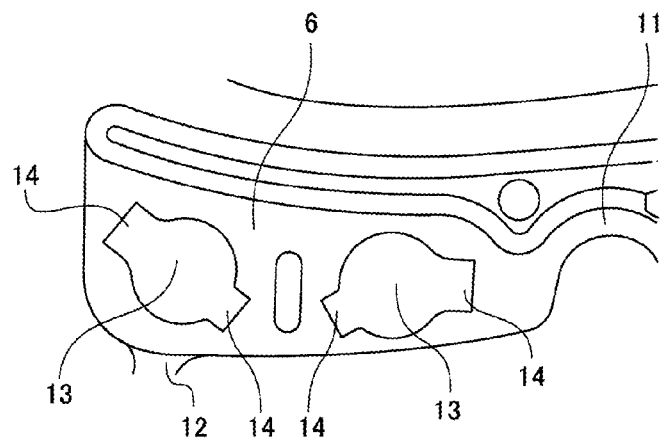

In the foregoing embodiments, the peeling portions 14 are provided for the respective reagent retaining portions 13. As shown in FIGS. 13(*a*), 13(*b*), and 13(*c*), two or more peeling portions 14 may be provided on each of the reagent retaining portions 13 as long as the peeling portion 14 is located on a part of the outer edge of the reagent retaining portion 13.

INDUSTRIAL APPLICABILITY

The present invention contributes to improvement of reliability of various component analyses using analyzing devices.

The invention claimed is:

1. An analyzing device comprising a main unit case containing:
   a feed passage having a microchannel structure for transporting a liquid to be tested to a measuring chamber from a sample feed opening provided on the main unit case;
   a separating chamber containing a reagent that treats a component of the liquid to be tested;
   a reservoir connected to the separating chamber via a first branch; and
   a measuring chamber connected to the separating chamber via a second branch,
   a reagent retaining portion disposed in the separating chamber, the reagent retaining portion having a top surface and being circular or substantially circular when viewed from above the top surface, the reagent being disposed on the reagent retaining portion, the reagent retaining portion having an inner edge positioned closer to a center of the separating chamber and an outer edge positioned further away from the center of the separating chamber, and
   a peeling portion connected to the outer edge of the reagent retaining portion and extending away from the center of the separating chamber, a top surface of the peeling portion being level with the top surface of the reagent retaining portion,
   wherein the analyzing device is used for centrifugally transporting the liquid treated by the reagent in the separating chamber to the measuring chamber, and for measurement of the liquid treated by the reagent.

2. The analyzing device according to claim 1, wherein the peeling portion is one of circular and substantially circular, one of triangular and substantially triangular, or one of rectangular and substantially rectangular in a plan view.

3. The analyzing device according to claim 1, wherein the reagent retaining portion protrudes downward from a ceiling of the separating chamber.

4. The analyzing device according to claim 1, wherein the reagent retaining portion is recessed upward from a ceiling of the separating chamber.

5. The analyzing device according to claim 1, wherein the reagent on the reagent retaining portion is a separating reagent, and the measuring chamber contains a reactant.

6. The analyzing device according to claim 1, further comprising an additional peeling portion positioned on an opposite side of the reagent retaining portion relative to the peeling portion and connected to the inner edge of the reagent retaining portion, wherein the area of the peeling portion is greater than the area of the additional peeling portion.

* * * * *